United States Patent [19]

Fried

[11] Patent Number: 5,256,819
[45] Date of Patent: Oct. 26, 1993

[54] PREPARATION OF POLYOXYALKYLENE-ALPHA, OMEGA-DICARBOXYLIC ACIDS

[75] Inventor: Herbert E. Fried, Houston, Tex.

[73] Assignee: Shell Oil Company, Houston, Tex.

[21] Appl. No.: 996,268

[22] Filed: Dec. 24, 1992

[51] Int. Cl.$^5$ .................... C07C 51/16; C07C 51/235
[52] U.S. Cl. ................................. 562/537; 562/538
[58] Field of Search ........................... 562/537, 538

[56] References Cited

U.S. PATENT DOCUMENTS

| | | | |
|---|---|---|---|
| 3,256,916 | 3/1981 | Morris et al. | 260/531 R |
| 3,929,873 | 12/1975 | Gammans | 260/531 R |
| 4,620,033 | 10/1986 | Isshiki et al. | 562/519 |
| 5,136,101 | 8/1992 | Fried | 568/402 |
| 5,136,102 | 8/1992 | Fried | 568/402 |
| 5,136,103 | 8/1992 | Fried | 568/402 |
| 5,155,278 | 10/1992 | Fried | 568/471 |
| 5,155,279 | 10/1992 | Fried | 568/471 |
| 5,175,359 | 12/1992 | Fried | 562/537 |

FOREIGN PATENT DOCUMENTS

| | | |
|---|---|---|
| 2854646 | 6/1979 | Fed. Rep. of Germany. |
| 3209434 | 9/1983 | Fed. Rep. of Germany. |
| 50-96516 | 7/1975 | Japan. |
| 1479735 | 3/1967 | U.S.S.R.. |
| 707907 | 1/1980 | U.S.S.R.. |

OTHER PUBLICATIONS

Miyazawa et.al., "Oxidation of Benzyl Alcohol with Iron (III) Using Polymers Containing Nitroxyl Radical Structure as a Mediator," J. Polym. Chem. Ed., 23 (9), 1985, pp. 2487-2494.

Grigor'ev et al., "Participation of Nitroxyl Radical in the Oxidation of Aldehyde and Alcohol Groups in 3-imidazolin-1-oxyls," Izc. AKad. Nauk SSSR, Ser. Khim., (1), 1978, pp. 208-210.

Miyazawa et al., "Oxidation of Benzyl Alcohol with Copper(II) Mediated by a Polymeric Oxoaminium Salt," J. Mol. Catal., 49(1), 1988, pp. 131-134.

Ganem et al., "Biological Spin Labels as Organic Reagents. Oxidation of Alcohols to Carbonyl Compounds Using Nitroxyls," J. Org. Chem., 40(13), 1975, pp. 1998-2000.

Miyazawa et al., "Oxidation of Benzyl Alcohol by Iron-(III) Mediated by Nitroxyl Radical," J. Mol. Catal., 31(2), 1985, pp. 217-220.

Anelli et al., "Fast and Selective Oxidation of Primary Alcohols to Aldehydes or to Carboxylic Acids and of Secondary Alcohols to Ketones Mediated by Oxoammonium Salts under Two-Phase Conditions," J. Org. Chem., 52 (12), pp. 2559-2562 (1985).

Inokuchi et al., "A Selective and Efficient Method for Alcohol Oxidations Mediated by N-Oxoammonium Salts in Combination with Sodium Bromite," J. Org. Chem., 1990, 55, pp. 462-466.

Organic Synthesis, vol. 69, p. 212 (1990).

Semmelhack et al., "Oxidation of Alcohols to Aldehydes with Oxygen and Cupric Ion, Mediated by Nitrosonium Ion," J. Am. Chem. Soc. 1984, 106, 3374-3376.

Yamaguchi et al., "Application of Redox System Based on Nitroxides to Organic Synthesis," Pure & Applied Chemistry, vol. 62(2), 1990, 217-222.

Primary Examiner—Arthur C. Prescott
Attorney, Agent, or Firm—Pamela J. McCollough

[57] ABSTRACT

A process for the preparation of a polyoxyalkylene-alpha,omega-dicarboxylic acid by reacting the corresponding polyoxyalkylene glycol with a stable free radical nitroxide in the presence of a $NO_x$-generating compound and optionally, an oxidant and/or a solvent, at a temperature in the range of from about 0° C. to about 100° C. and thereafter separating out the polyoxyalkylene-alpha,omega-dicarboxylic acid.

22 Claims, No Drawings

PREPARATION OF POLYOXYALKYLENE-ALPHA, OMEGA-DICARBOXYLIC ACIDS

FIELD OF THE INVENTION

This invention relates to a process for the preparation of polyoxyalkylene-alpha,omega-dicarboxylic acids by the oxidation of the corresponding polyoxyalkylene glycols in the presence of a stable free radical nitroxide and a $NO_x$-generating compound.

BACKGROUND OF THE INVENTION

Dicarboxylic acids are useful as chelating agents, detergent builders, and emulsifying agents. These acids, being composed of only the elements C, H and O, do not pose the environmental problems that other compounds containing heteroatoms such as N, S, and P pose. The alpha,omega-dicarboxylic acids can be prepared in a two-step process by first reacting a glycol with ethylene oxide and an alkaline catalyst and thereafter converting the polyoxyalkylene glycol to a polyoxyalkylene-alpha,omega-dicarboxylic acid.

Japanese Patent No. 50-96516, issued July 31, 1975, discloses a process for the preparation of carboxylic acid salts by the liquid phase dehydrogenation of alcohols with caustic alkali in the presence of precious metal catalysts, including palladium. This process uses a relatively high temperature, 100° C.-270° C. These high temperatures can degrade the ether linkages especially in the highly ethoxylated alcohols.

It is known to use nitroxyl radicals/oxoammonium salts in the oxidation of primary alcohols to produce aldehydes and acids and secondary alcohols to ketones. *Journal of Organic Chemistry*, vol. 52 (12), pp. 2559-2562; *Pure and Applied Chemistry*, vol. 62(2), 1990, pp. 217-222; *Journal of Organic Chemistry*, Vol. 55, 1990, pp. 462-466. The primary products produced in these processes are aldehydes and the stoichiometrically consumed oxidant is hypochlorite.

It is generally more difficult to oxidize polyoxyalkylene glycols than alkanols as it is difficult to oxidize polyoxyalkylene glycols without splitting the molecular chain at the ether linkage thereby producing a large proportion of undesired by-products.

It is therefore an object of this invention to produce polyoxyalkylene-alpha,omega-dicarboxylic acids in high yields and with high selectivities from polyoxyalkylene glycols without producing large amounts of other products such as oxalic acid and glycolic acid.

It has been found that polyoxyalkylene-alpha,omega-dicarboxylic acids can be produced in high yields and with high selectivities by using a stable free radical nitroxide and a $NO_x$-generating compound and an optionally, oxidant and/or a solvent.

SUMMARY OF THE INVENTION

This invention relates to a process for the preparation of a polyoxyalkylene-alpha,omega-dicarboxylic acid of the formula:

$$HO_2CCH_2O(CH_2CHR'O)_nCH_2CO_2H$$

wherein R' is hydrogen or methyl or mixtures thereof (on the individual molecule) and n is an integer of from 0 to about 5,000 which comprises reacting the corresponding polyoxyalkylene glycol with a stable free radical nitroxide having the formula:

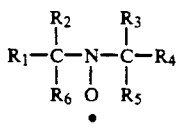

wherein (1) (a) each of $R_1$, $R_2$ $R_3$ and $R_4$ is an alkyl, aryl or heteroatom substituted alkyl group having 1 to about 15 carbon atoms, and (b) $R_5$ and $R_6$ (i) each is an alkyl group having 1 to about 15 carbon atoms provided that $R_1$-$R_6$, are not all alkyl groups, or a substituted alkyl group having 1 to about 15 carbon atoms wherein the substituent is hydrogen, cyano, $-CONH_2$, $-OCOCH$, $OCOC_2H_5$, carbonyl, alkenyl wherein the double bond is not conjugated with the nitroxide moiety, or $-COOR$ wherein R of the $-COOR$ group is alkyl or aryl, or (ii) together form part of a ring having at least two carbon atoms and up to two heteroatoms of O or N, or (2) the

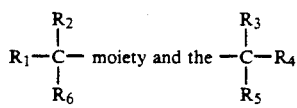

moiety individually are aryl, in the presence of a $NO_x$-generating compound and optionally, an oxidant and/or a solvent, at a temperature in the range of from about 0° C. to about 100° C. and thereafter separating out the polyoxyalkylene-alpha,omega-dicarboxylic acid.

DESCRIPTION OF THE PREFERRED EMBODIMENTS

The present process converts polyoxyalkylene glycols of the formula $$HOCH_2CH_2O(CH_2CHR'O)_nCH_2CH_2OH \quad (I)$$

wherein R' is hydrogen or alkyl, preferably methyl, or mixtures thereof (on the individual molecule) and n represents the average number of oxyalkylene groups and is an integer of from 0 to about 5,000, preferably from about 10 to about 500, and more preferably about 20 to about 200, to the corresponding polyoxyalkylene-alpha,omega-dicarboxylic acids of the formula:

$$HO_2CCH_2O(CH_2CHR'O)_nCH_2CO_2H \quad (II)$$

by contacting the polyoxyalkylene glycol with a stable free radical nitroxide in the presence of a $NO_x$-generating compound and optionally, an oxidant and/or a solvent, at a temperature in the range of from about 0° C. to about 100° C. and thereafter separating out the polyoxyalkylene-alpha,omega-dicarboxylic acid.

The polyoxyalkylene glycol reactant suitably comprises one or more polyoxyalkylene glycols having a molecular weight in the range of from about 100 to about 250,000, preferably from about 500 to about 20,000, and more preferably from about 1,000 to about 10,000. The polyoxyalkylene glycols are typically prepared by the reaction of a glycol with an alkylene oxide in the presence of a suitable alkoxylation catalyst.

Glycols suitable for use in preparing the polyoxyalkylene glycol reactant in the present invention include ethylene glycol, diethylene glycol and triethylene glycol. In addition, glycols prepared by reacting ethylene oxide with water are also suitable for use in preparing the polyoxyalkylene glycol reactant in the present process. Specific glycols and glycol mixtures which are suitable for use in preparing the alkoxyalkanol reactant are well known and are commercially available.

Suitable examples of polyoxyalkylene glycols for use in the present invention which are commercially available include poly(ethylene glycol) having a molecular weight of 10,000, poly(ethylene glycol) having a molecular weight of 8,000, poly(ethylene glycol) having a molecular weight of 3,400, poly(ethylene glycol) having a molecular weight of 2,000, poly(ethylene glycol) having a molecular weight of 1,500, poly(ethylene glycol) having a molecular weight of 1,000, poly(ethylene glycol) having a molecular weight of 900, poly(ethylene glycol) having a molecular weight of 600, poly(ethylene glycol) having a molecular weight of 400, poly(ethylene glycol) having a molecular weight of 300, poly(ethylene glycol) having a molecular weight of 200 and mixtures thereof. In a preferred embodiment, the polyoxyalkylene glycol has a molecular weight of up to about 10,000. In a particularly preferred embodiment, the polyoxyalkylene glycol has a molecular weight of from about 2,000 to about 10,000.

The process of the instant invention is particularly suited to alkoxylated glycols. In the case of propoxylated or alkoxylated glycols, it is necessary to further ethoxylate in order to obtain oxyalkylene-alpha,omega-dicarboxylic acids. The R' groups on an individual molecule can be hydrogen, methyl or mixtures thereof. For example, straight ethoxylated, straight propoxylated and mixed ethoxylated-propoxylated detergent range glycols are commercially available.

The term "stable free radical nitroxide" as used herein shall mean a free radical nitroxide that can be prepared by conventional chemical methods and will exist long enough to be used in a subsequent chemical reaction or examined in a static system by normal methods of spectroscopy. Generally, the stable free radical nitroxides of the present invention have a half life of at least one year. The term "stable free radical" shall also be understood to include the precursor to a stable free radical from which the stable free radical may be produced in situ.

The stable free radical nitroxides, as used in the present process, are precursors to catalysts, i.e., oxoammonium salts, active for the oxidation of glycols to the corresponding dicarboxylic acids. These catalysts are generated in situ by the oxidation of a stable free radical nitroxide to an oxoammonium salt with an oxygen-containing oxidant. The stable free radical nitroxide can be obtained by the oxidation of secondary amines or hydroxylamines.

The stable free radical nitroxides which are suitable for use in the instant invention have the formula:

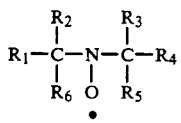
(III)

wherein each of $R_1$, $R_2$, $R_3$ and $R_4$ is an alkyl, aryl or heteroatom substituted alkyl groups and no hydrogen is bound to the remaining valences on the carbon atoms bound to the nitrogen. As used herein, the term "alkyl" is meant to include cycloalkyl. The alkyl (or heteroatom substituted) groups R1-R4 may be the same or different, and preferably contain 1 to 15 carbon atoms. Preferable, $R_1$-$R_4$ are methyl, ethyl, or propyl groups. In addition to hydrogen, the heteroatom substituents may include, halogen, oxygen, nitrogen and the like.

The remaining valences ($R_5$ and $R_6$) in formula III above may be satisfied by any atom or group except hydrogen which can bond covalently to carbon, although some groups may reduce the stabilizing power of the nitroxide and are undesirable. When $R_1$, $R_2$, $R_3$ and $R_4$ are each alkyl groups, however, at least one of $R_5$ and $R_6$ must be an aryl group. Preferably, $R_5$ and $R_6$ are substituted alkyl groups having 1 to about 15 carbon atoms wherein the substituent is selected from halogen, cyano, —COOR, wherein R is alkyl or aryl, —CONH$_2$, —OCOC$_2$H$_5$, carbonyl, or alkenyl where the double bond is not conjugated with the nitroxide moiety, or alkyl groups of 1 to about 15 carbon atoms. $R_5$ and $R_6$ together may also form a ring of at least two carbon atoms and up to two heteroatoms, such as O or N. Examples of suitable compounds having the structure above and in which $R_5$ and $R_6$ form part of the ring are piperidinyl-1-oxyls and pyrrolidin-1-oxyls.

The

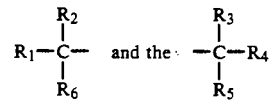

moieties in formula III above can individually be aryl, i.e.,

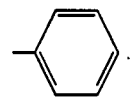

Examples of suitable compounds having the structure above in which the

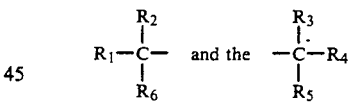

moieties are individually aryl are diphenylamine, phenyl tertiary butylamine 3-methyl-diphenylamines, 2-chlorophenylamine and the like. These compounds may be substituted with an substituents which do not interfere with the reaction.

In a preferred embodiment, the stable free radical nitroxide has the formula:

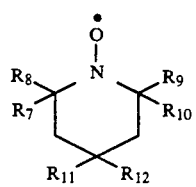

wherein each of $R_7$, $R_8$, $R_9$ and $R_{10}$ is an alkyl, aryl or heteroatom substituted alkyl group having 1 to about 15 carbon atoms and no hydrogen is bound to the remaining valences on the carbon atoms bound to the nitrogen, and each of $R_{11}$ and $R_{12}$ is alkyl, hydrogen, aryl or a substituted heteroatom. As used herein, the term "alkyl" is meant to include cycloalkyl. The alkyl (or heteroatom substituted) groups $R_7-R_{10}$ may be the same or different, and preferably contain 1 to 15 carbon atoms. Preferably, $R_7-R_{10}$ are methyl, ethyl, or propyl groups. In addition to hydrogen, the heteroatom substituents may include, halogen, oxygen, nitrogen and the like. Preferably, one of $R_{11}$ and $R_{12}$ is hydrogen, with the other one being a substituted heteroatom which does not interfere with the reaction. Suitable substituted heteroatoms include

$-O-SO_3H$, $-O-$polymer and the like.

In a particularly preferred embodiment, the nitroxide is selected from the group consisting of 2,2,6,6-tetramethyl-piperidine-1-oxyl, 4-hydroxy-2,2,6,6-tetramethyl-piperidine-1-oxyl, 4-pivoylamido-2,2,6,6-tetramethyl-piperidine-1-oxyl-4-sulfate, 4-alkoxy-2,2,6,6-tetramethyl-piperidine-1-oxyl, and mixtures thereof, with 2,2,6,6-tetramethyl-piperidine-11-oxyl, 4-pivoylamido-2,2,6,6-tetramethyl-piperidine-1-oxyl, and 4-alkoxy-2,2,6,6-tetramethyl-piperidine-1-oxyl being especially preferred.

The $NO_x$-generating compound in the present process is typically selected from the group consisting of an alkali metal nitrosodisulfonate, nitric acid and mixtures thereof, with nitric acid being preferred. However, any compound which serves to generate $NO_x$ during the course of the reaction and which does not interfere with the reaction would be suitable. While not wishing to be bound by any particular theory, it is believed that nitrogen oxides ($NO_x$) are generated in the reaction and are the active species in the reaction.

The alkali metal nitrosodisulfonate suitable for use as a $NO_x$-generating compound can be any alkali metal nitrosodisulfonate although potassium nitrosodisulfonate is preferred. As used herein, the term "alkali metal" is used as a descriptor of the elements Group IA of the Periodic Table of the Elements (Li, Na, K, Rb, Cs, Fr). The alkali metal nitrosodisulfonate is typically dissolved in water prior to being added to the reaction mixture although it can be added as a solid after all of the other reactants have been added.

As used herein, the term "nitric acid" refers to nitric acid, fuming nitric acid or nitrous acid generated by contacting a nitrate or nitrite salt such as, for example, an alkali metal salt, a tetraalkylammonium salt, an alkaline earth salt or a rare earth salt, with a strong acid such as, for example, a mineral acid. The nitric acid suitable for use as a $NO_x$-generating compound in the present invention typically has a concentration in the range of from about 50 percent to about 100 percent, preferably about 70 percent. Generally, an amount of nitric acid in the range of from about 5 mole percent to about 1,000 mole percent, basis the moles of starting polyoxyalkylene glycol is utilized. The nitric acid is typically added to the reaction mixture after all of the other reactants have been added.

In a preferred embodiment, an oxidant is also added as a reactant. In general, when catalytic amounts of the $NO_x$-generating compound and nitroxide are used, the addition of an oxidant is preferred, whereas when stoichiometric amounts of the $NO_x$-generating compound and nitroxide are used, an oxidant may not be needed. One skilled in the art could readily determine by routine experimentation whether or not an oxidant would be useful in the reaction. The oxidants suitable for use in the instant invention are those compounds which are capable, in the presence of a $NO_x$-generating compound, of oxidizing the stable free radical nitroxide to the oxoammonium salt. Suitable oxidants include oxygen-containing gases such as pure oxygen and oxygen in air. Whereas pure oxygen can is preferred to accomplish the desired conversion, the oxygen can also be diluted with an inert gas such as nitrogen, helium, argon, or other similar gas. While air can be used as the oxidant, the reaction rate is much slower. For purposes of increasing the reaction rate, higher $O_2$ pressures such as, for example, 1000 psig can be utilized. In a preferred embodiment, pure oxygen is used as the oxidant and it is bubbled into the reaction solution.

The reaction is preferably carried out in the presence of a solvent. When the molecular weight is such that the alkoxyalkanol reactant is a solid or a viscous liquid, a solvent in which the solid or highly viscous alkoxyalkanol reactant is soluble must be added. Suitable solvents are thus those in which the alkoxyalkanol reactant is soluble and those which do not interfere with the reaction. Suitable solvents include dichloromethane, triglyme, tertiary butyl alcohol, acetonitrile, carbon tetrachloride, monoglyme, diglyme, tertiary amyl alcohol and the like, and mixtures thereof. In a preferred embodiment, the solvent is selected from the group consisting of dichloromethane, acetonitrile, tertiary butyl alcohol and mixtures thereof. The weight ratio of solvent to alkoxyalkanol reactant is typically in the range of from about 1:1 to about 1:100, and preferably in the range of from about 1:1 to about 1:5.

The amounts and concentrations of the reactants utilized in the process of the instant invention can vary within wide ranges. The amount of stable free radical nitroxide is typically in the range of from about 1 mole percent to about 500 mole percent, preferably from about 5 mole percent to about 20 mole percent, basis the number of moles starting polyoxy- alkylene glycol. Generally, the amount of $NO_x$-generating compound used is in the range of from about 5 mole percent to about 1000 mole percent, basis the number of moles of polyoxyalkylene glycol.

The process of the present invention is typically conducted under mild conditions, with good results being obtained using a temperature in the range of from about 0° C. to about 100° C., preferably about 20° C. to about 70° C., and most preferably, about 40° C. to about 60° C. Reaction pressures are not critical although higher pressures can result in increased reaction rates. Pressures in the range of from about atmospheric pressure up to about 1000 psig can be employed with good results.

The process of the instant invention can be carried out either batchwise or continuously, using a stirrer equipped reactor or other well known contacting technique to achieve adequate mixing. Preferred reaction conditions, e.g., temperature, pressure, flow rates, etc., vary somewhat depending on the specific nitroxide utilized and on the concentration of the nitroxide.

The process of the instant invention can be carried out in a variety of ways. For example, 0.0032 moles of the polyoxyalkylene glycol and 0.0064 moles of the nitroxide may be added to the reaction vessel, followed by the addition of 0.011 moles of 70 percent nitric acid. Following the reaction, the product may be separated from the reaction mixture using conventional procedures such as, for example, an extraction procedure or a precipitation procedure. The particular procedure utilized depends on whether the reaction product is a solid or liquid at room temperature. If the product is solid at room temperature, precipitation is typically used. If, however, the product is a liquid at room temperature, an extraction procedure is generally used. The reaction product can be purified by a number of conventional means such as high temperature water washing or catalytic hydrogenation.

Depending upon process conditions and the nitroxide used, the yields of polyoxyalkylene-alpha,omega-dicarboxylic acid obtained by this invention can be greater than about 98% of starting material being converted. The products produced by the instant process can be used in a variety of applications. For example, corrosion inhibitors, detergent builders or emulsifying agents.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The process of this invention will be further described by the following embodiments which are provided for illustration and are not to be construed as limiting the invention.

ILLUSTRATIVE EMBODIMENTS

Example 1

10.9 Grams of poly(ethylene glycol) having a molecular weight of 3400, 1.0 grams of 2,2,6,6-tetramethyl-piperidine-1-oxyl, 50 milliliters of acetonitrile and 1 gram of 70 percent nitric acid were charged to a 100 milliliter round bottomed flask. $O_2$ was bubbled through this mixture at ambient pressure. The reaction temperature was held at 35° C. over a 6-hour period. The results are presented in Table I.

Example 2

100 Grams of poly(ethylene glycol) having a molecular weight of 3400, 5 grams of 2,2,6,6-tetramethyl-piperidine-1-oxyl, 200 milliliters of methylene chloride and 5 grams of 70 percent nitric acid were charged to a 500 milliliter round bottomed flask. Air was bubbled through this mixture at ambient pressure. The reaction was held at reflux over a 8-hour period. The results are presented in Table I.

Example 3

10.9 Grams of poly(ethylene glycol) having a molecular weight of 3400, 1 gram of 2,2,6,6-tetramethyl-piperidine-1-oxyl, 50 milliliters of acetonitrile and 1 gram of 70 percent nitric acid were charged to a 100 milliliter round bottomed flask. The reaction mixture was held open to the atmosphere. The reaction temperature was held at 35° C. over a 6-hour period. The results are presented in Table I.

Example 4

10.9 Grams of poly(ethylene glycol) having a molecular weight of 3400, 0.2 grams of 2,2,6,6-tetramethyl-piperidine-1-oxyl, 50 milliliters of methylene chloride and 0.2 grams of 70 percent nitric acid were charged to a 100 milliliter round bottomed flask. $O_2$ was bubbled through this mixture at ambient pressure. The reaction temperature was held at 35° C. over a 5-hour period. The results are presented in Table I.

Comparative Example A

Comparative Example A was carried out in a manner similar to Example 1 except that no nitroxide was used. The results are presented in Table I.

Comparative Example B

Comparative Example B was carried out in a manner similar to Example 4 except that no nitric acid was used. The results are presented in Table I.

Comparative Example C

Comparative Example C was carried out in a manner similar to Example 4 except that no nitroxide was used. The results are presented in Table I.

As can be seen in Table I, nitroxide and nitric acid are necessary for the oxidation of the terminal diol to proceed.

TABLE I

Oxidation Of Polyoxyalkylene Glycols to Polyoxyalkylene-Alpha-Omega Dicarboxylic Acids

| | % Conversion | % Selectivity to Dicarboxylic Acids |
|---|---|---|
| Example 1 | >99 | >99 |
| Example 2 | >99 | >99 |
| Example 3 | >99 | >99 |
| Example 4 | 56 | >99 |
| Comparative Example A | 0 | 0 |
| Comparative Example B | 0 | 0 |
| Comparative Example C | 0 | 0 |

What is claimed is:

1. A process for the preparation of a polyoxyalkylene-alpha,omega-dicarboxylic acid of the formula

$$HO_2CCH_2O(CH_2CHR'O)_nCH_2CO_2H$$

wherein R' is hydrogen or methyl or mixtures thereof (on the individual molecule) and n is an integer of from 0 to about 5,000, which comprises reacting the corresponding polyoxyalkylene glycol with a stable free radical nitroxide having the formula:

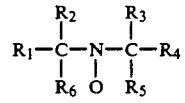

wherein (1) (a) each of $R_1$, $R_2$, $R_3$ and $R_4$ is an alkyl, aryl or heteroatom substituted alkyl group having 1 to about 15 carbon atoms, and (b) $R_5$ and $R_6$ (i) each is an alkyl group having 1 to about 15 carbon atoms provided that R1-R6 are not all alkyl groups, or a substituted alkyl group having 1 to about 15 carbon atoms wherein the substituent is hydrogen, cyano, —CONH —OCOCH, $OCOC_2H_5$, carbonyl, alkenyl wherein the double bond is not conjugated with the nitroxide moiety, or —COOR wherein R of the —COOR group is alkyl or aryl, or (ii) together form part of a ring having at least two carbon atoms and up to two heteroatoms of O or N, or (2) the

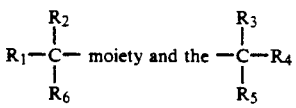

moiety individually are aryl, in the presence of a NO$_x$-generating compound and an oxidant at a temperature in the range of from about 0° C. to about 100° C. and thereafter separating out the polyoxyalkylene-alpha,omega-dicarboxylic acid.

2. The process of claim 1 wherein the stable free radical nitroxide has the formula:

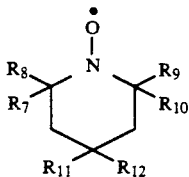

wherein each of $R_7$, $R_8$, $R_9$ and $R_{10}$ is an alkyl, aryl or heteroatom substituted alkyl group having 1 to about 15 carbon atoms and each of $R_{11}$ and $R_{12}$ is alkyl, hydrogen, aryl or a substituted heteroatom.

3. The process of claim 2 wherein the stable free radical nitroxide is selected from the group consisting of 2,2,6,6-tetramethyl-piperidine-1-oxyl,4-hydroxy-2,2,6,6-tetramethyl-piperidine-1-oxyl,4-pivoylamido-2,2,6,6-tetramethyl-piperidine-1-oxyl, 4-alkoxy-2,2,6,6-tetramethyl-piperidine and mixtures thereof.

4. The process of claim 3 wherein the stable free radical nitroxide is selected from the group consisting of 2,2,6,6-tetra methyl-piperidine-1-oxyl,4-pivoylamido-2,2,6,6-tetramethyl-piperidine-1-oxyl, 4-alkoxy-2,2,6,6-tetramethyl-piperidine-1-oxyl and mixtures thereof.

5. The process of claim 1 wherein said NO$_x$-generating compound is selected from the group consisting of nitric acid, an alkali metal nitrosodisulfonate and mixtures thereof.

6. The process of claim 5 wherein said NO$_x$-generating compound is nitric acid.

7. The process of claim 6 wherein said nitric acid has a concentration in the range of from about 50 percent to about 100 percent.

8. The process of claim 7 wherein said nitric acid has a concentration of about 70 percent.

9. The process of claim 5 wherein said NO$_x$-generating compound is an alkali metal nitrosodisulfonate.

10. The process of claim 9 wherein said alkali metal nitrosodisulfonate is potassium nitrosodisulfonate.

11. The process of claim 1 wherein the amount of NO$_x$-generating compound is in the range of from about 5 mole percent to about 1,000 mole percent, basis the number of moles polyoxyalkylene glycol.

12. The process of claim 1 wherein said polyoxyalkylene glycol is contacted with said stable free radical nitroxide, followed by the addition thereto of said NO$_x$-generating compound and said oxidant.

13. The process of claim 12 wherein the amount of stable free radical nitroxide is in the range of from about 1 mole percent to about 500 mole percent, basis the number of moles of polyoxyalkylene glycol.

14. The process of claim 13 wherein the amount of stable free radical nitroxide is in the range of from about 5 mole percent to about 20 mole percent, basis the number of moles of polyoxyalkylene glycol.

15. The process of claim 12 wherein the amount of NO$_x$-generating compound is in the range of from about,5 mole percent to about 1000 mole percent, basis the number of moles of polyoxyalkylene glycol.

16. The process of claim 1 wherein said oxidant is an oxygen-containing gas.

17. The process of claim 16 wherein said oxygen containing gas is selected from the group consisting of pure oxygen and air.

18. The process of claim 17 wherein said oxygen-containing gas is pure oxygen.

19. The process of claim 1 wherein said process is carried out in the presence of a solvent.

20. The process of claim 19 wherein said, solvent is selected from the group consisting of dichloromethane, triglyme, tertiary butyl alcohol, acetonitrile, carbon tetrachloride, monoglyme, diglyme, tertiary amyl alcohol and mixtures thereof.

21. The process of claim 1 wherein said process is carried out at a temperature in the range of from about 20° C. to about 70° C. and at atmospheric pressure.

22. The process of claim 19 wherein said process is carried out at a temperature in the range of from about 40° C. to about 60° C. and at atmospheric pressure.

* * * * *